United States Patent
Phan et al.

(10) Patent No.: US 6,673,774 B2
(45) Date of Patent: Jan. 6, 2004

(54) 11-O-SUBSTITUTED MACROLIDES AND THEIR DESCLADINOSE DERIVATIVES

(75) Inventors: Ly Tam Phan Phan, Malden, MA (US); Deqiang Niu, Waltham, MA (US); Yat Sun Or, Cambridge, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/011,322

(22) Filed: Dec. 3, 2001

(65) Prior Publication Data
US 2003/0114396 A1 Jun. 19, 2003

(51) Int. Cl.$^7$ .......................... A61K 31/70; C07M 17/08
(52) U.S. Cl. ............................ 514/29; 536/7.2; 536/7.4; 536/18.5
(58) Field of Search .................... 536/7.2, 7.5, 18.5; 514/29

(56) References Cited

U.S. PATENT DOCUMENTS

| | | | |
|---|---|---|---|
| 3,883,507 A | 5/1975 | Reimann et al. | 260/210 |
| 4,847,242 A | 7/1989 | Davies | 514/29 |
| 6,028,181 A * | 2/2000 | Or et al. | 536/7.2 |

FOREIGN PATENT DOCUMENTS

| | | |
|---|---|---|
| EP | 0194833 A2 | 9/1986 |
| EP | WO98/38199 | 9/1998 |

* cited by examiner

Primary Examiner—Elli Peselev
(74) Attorney, Agent, or Firm—Gaetano D. Maccarone; Jason D. Ferrone

(57) ABSTRACT

There are described 11-O-substituted macrolides and their descladinose derivatives and pharmaceutically acceptable compositions comprising a therapeutically effective amount of a compound of the invention in combination with a pharmaceutically acceptable carrier. Also described is a method for treating bacterial infections by administering to a mammal a pharmaceutical composition containing a therapeutically-effective amount of a compound of the invention, and processes for the preparation of such compounds.

9 Claims, No Drawings

11-O-SUBSTITUTED MACROLIDES AND THEIR DESCLADINOSE DERIVATIVES

TECHNICAL FIELD

The present invention relates to novel macrolides having antibacterial activity and useful in the treatment and prevention of bacterial infections. More particularly, the invention relates to a novel class of 11-O-substituted Clarithromycin derivatives, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin and clarithromycin.

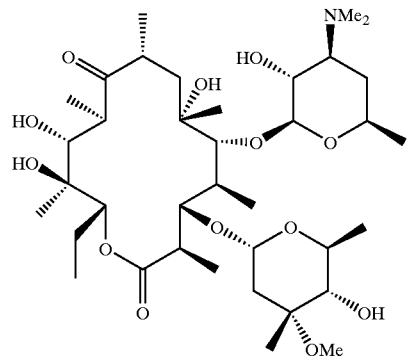

Erythromycin

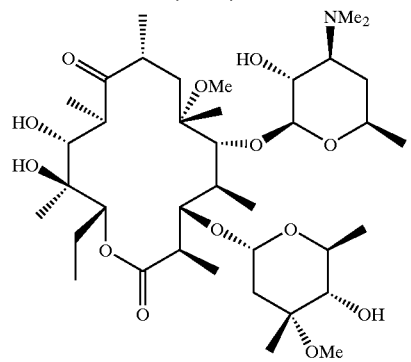

Clarithromycin

The search for macrolides active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

SUMMARY OF THE INVENTION

The present invention provides a novel class of 11-O-substituted derivatives of erythromycin with the general formulae (I) and (II), as well as the pharmaceutically acceptable salts, esters and prodrugs thereof.

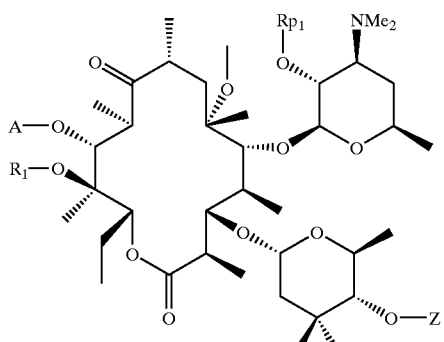

(I)

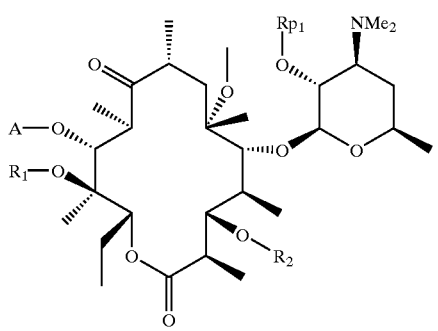

(II)

In formulae (I) and (II) above,
A is selected from the group consisting of:
(1) $C_1$–$C_6$-alkyl, $C_2$–$C_6$-alkenyl or $C_2$–$C_6$-alkynyl, optionally substituted with one or more substituents selected from the group consisting of:
  i. halogen;
  ii. aryl;
  iii. substituted aryl;
  iv. heteroaryl;
  v. substituted heteroaryl;
  vi. —O—$R_5$, where $R_5$ is selected from the group consisting of:
    a. hydrogen;
    b. aryl;
    c. substituted aryl;
    d. heteroaryl; and
    e. substituted heteroaryl; and
  vii. —O—$C_1$–$C_6$-alkyl-$R_5$, where $R_5$ is as previously defined;
  viii. —O—$C_2$–$C_6$-alkenyl-$R_5$, where $R_5$ is as previously defined;
  ix. —O—$C_2$–$C_6$-alkynyl-$R_5$, where $R_5$ is as previously defined; and
  x. —$NR_6R_7$, where $R_6$ and $R_7$ are each independently selected from hydrogen, $C_1$–$C_6$-alkyl, optionally substituted with one or more substituents selected from the group consisting of halogen, aryl, substituted aryl, heterocyclic and substituted heterocyclic, $C_2$–$C_6$-alkenyl, optionally substituted with one or more substituents selected from the group consisting of halogen, aryl, substituted aryl, heterocyclic and substituted heterocyclic, $C_2$–$C_6$-alkynyl, optionally substituted with one or more substituents selected from the group consisting of halogen, aryl, substituted aryl, heterocyclic and substituted heterocyclic or $R_6R_7$ taken with the nitrogen atom to which they are connected form a 3- to 7-membered ring which may optionally contain one or more hetero functions selected from the group consisting of —O—, —NH—, —N($C_1$–$C_6$-alkyl)-, —N(aryl)-, —N(heteroaryl)-, —S—, —S(O)— and —S(O)$_2$—;

(2) —C(O)—$R_5$, where $R_5$ is as previously defined;

(3) —C(O)—$C_1$–$C_6$-alkyl-$R_5$, where $R_5$ is as previously defined;

(4) —C(O)—$C_2$–$C_6$-alkenyl-$R_5$, where $R_5$ is as previously defined;

(5) —C(O)—$C_2$–$C_6$-alkynyl-$R_5$, where $R_5$ is as previously defined;

(6) —$C_1$–$C_6$-alkyl-M—$R_5$, where M=—OC(O)—, —OC(O)O—, —OC(O)$NR_6$—, —$NR_6$C(O)—, —$NR_6$C(O)O—, —$NR_6$C(O)NR7-, —$NR_6$C(N)NR7-, S(O)$_n$—, where n=0, 1 or 2, and where $R_5$, $R_6$, $R_7$ are as previously defined;

(7) —$C_2$–$C_6$-alkenyl-M—$R_5$, where M=—OC(O)—, —OC(O)O—, —OC(O)$NR_6$—, —$NR_6$C(O)—, —$NR_6$C(O)O—, —$NR_6$C(O)$NR_7$—, —$NR_6$C(N)$NR_7$—, S(O)$_n$—, where n=0, 1 or 2, and where $R_5$, $R_6$, $R_7$ are as previously defined; and (8) —$C_2$–$C_6$-alkynyl-M—$R_5$, where M=—OC(O)—, —OC(O)O—, —OC(O)$NR_6$—, —$NR_6$C(O)—, —$NR_6$C(O)O—, —$NR_6$C(O)$NR_7$—, —$NR_6$C(N)$NR_7$—, S(O)$_n$-, where n=0, 1 or 2, and where $R_5$, $R_6$, $R_7$ are as previously defined;

$R_1$ is selected from the group consisting of:

(1) hydrogen;

(2) $R_3$, where $R_3$ is $C_1$–$C_6$-alkyl, $C_2$–$C_6$-alkenyl or $C_2$–$C_6$-alkynyl, optionally substituted with one or more substituents selected from the group consisting of:
  a. halogen;
  b. aryl;
  c. substituted-aryl;
  d. heteroaryl;
  e. substituted-heteroaryl;
  f. —O—$C_1$–$C_6$-alkyl-$R_5$, where $R_5$ is as previously defined;
  g. —$NR_6R_7$, where $R_6$ and $R_7$ are as previously defined.

(3) —C(=O)—$R_4$, where $R_4$ is H or $R_3$ as previously defined;

(4) —C(=O)O—$R_3$, where $R_3$ is as previously defined; and (5) —C(=O)N—$R_6R_7$, where $R_6$ and $R_7$ are as previously defined;

$R_2$ is selected from the group consisting of:

(1) hydroxy protecting group;

(2) $R_5$, as previously defined;

(3) —X—Y—$R_5$, where X=—C(O), —C(O)O—, —C(O)NH—, or absent, and Y=$C_1$–$C_6$-alkyl or absent, and $R_5$ is as previously defined; and (4) $C_1$–$C_6$-alkyl, $C_2$–$C_6$-alkenyl or $C_2$–$C_6$-alkynyl optionally substituted with one or more substituents selected from the group consisting of:
  a. halogen;
  b. aryl;
  c. substituted-aryl;
  d. heteroaryl;
  e. substituted-heteroaryl;
  f. —O—$R_5$ where $R_5$ is as previously defined;
  g. —O—$C_1$–$C_6$-alkyl-$R_5$ where $R_5$ is as previously defined;
  h. —O—$C_2$–$C_6$-alkenyl-$R_5$ where $R_5$ is as previously defined;
  i. —O—$C_2$–$C_6$-alkynyl-$R_5$ where $R_5$ is as previously defined; and
  j. —$NR_6R_7$ where $R_6$ and $R_7$ are as previously defined;

$Rp_1$ is hydrogen or hydroxy protecting group; and

Z is selected from the group consisting of:

(1) hydrogen;

(2) hydroxy protecting groups; and (3) —X—$R_3$, where X and $R_3$ are as previously defined.

In another aspect of the present invention are disclosed pharmaceutical compositions comprising a therapeutically effective amount of a compound of the invention in combination with a pharmaceutically acceptable carrier and treatment of bacterial infections with such compositions. Suitable carriers and methods of formulation are also disclosed. The compounds and compositions of the present invention have antibacterial activity.

In a further aspect of the present invention are provided processes for the preparation of macrolide derivatives of formulae (I) and (II) above.

DETAILED DESCRIPTION OF THE INVENTION

The present invention includes compounds represented by formulae (I) or (II), their pharmaceutical salts, esters or prodrugs thereof, as described above.

Representative compounds of the present invention include compounds illustrated below:

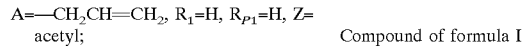

A=—$CH_2CH$=$CH_2$, $R_1$=H, $R_{P1}$=H, Z=acetyl;     Compound of formula I

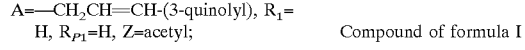

A=—$CH_2CH$=CH-(3-quinolyl), $R_1$=H, $R_{P1}$=H, Z=acetyl;     Compound of formula I

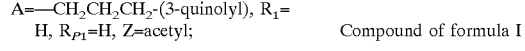

A=—$CH_2CH_2CH_2$-(3-quinolyl), $R_1$=H, $R_{P1}$=H, Z=acetyl;     Compound of formula I

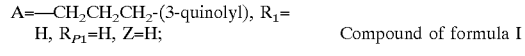

A=—$CH_2CH_2CH_2$-(3-quinolyl), $R_1$=H, $R_{P1}$=H, Z=H;     Compound of formula I

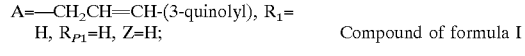

A=—$CH_2CH$=CH-(3-quinolyl), $R_1$=H, $R_{P1}$=H, Z=H;     Compound of formula I

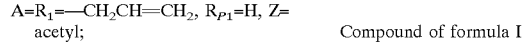

A=$R_1$=—$CH_2CH$=$CH_2$, $R_{P1}$=H, Z=acetyl;     Compound of formula I

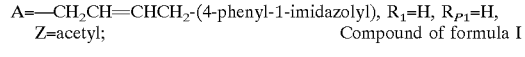

A=—$CH_2CH$=$CHCH_2$-(4-phenyl-1-imidazolyl), $R_1$=H, $R_{P1}$=H, Z=acetyl;     Compound of formula I

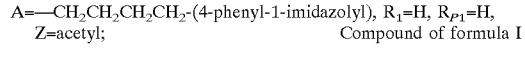

A=—$CH_2CH_2CH_2CH_2$-(4-phenyl-1-imidazolyl), $R_1$=H, $R_{P1}$=H, Z=acetyl;     Compound of formula I

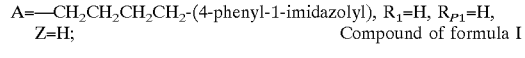

A=—$CH_2CH_2CH_2CH_2$-(4-phenyl-1-imidazolyl), $R_1$=H, $R_{P1}$=H, Z=H;     Compound of formula I

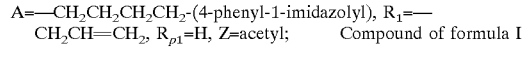

A=—$CH_2CH_2CH_2CH_2$-(4-phenyl-1-imidazolyl), $R_1$=—$CH_2CH$=$CH_2$, $R_{p1}$=H, Z=acetyl;     Compound of formula I

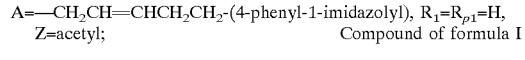

A=—$CH_2CH$=$CHCH_2CH_2$-(4-phenyl-1-imidazolyl), $R_1$=$R_{P1}$=H, Z=acetyl;     Compound of formula I

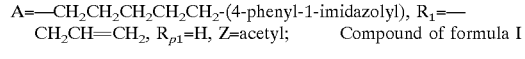

A=—$CH_2CH_2CH_2CH_2CH_2$-(4-phenyl-1-imidazolyl), $R_1$=—$CH_2CH$=$CH_2$, $R_{p1}$=H, Z=acetyl;     Compound of formula I

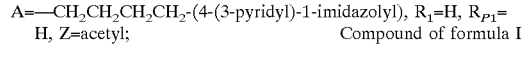

A=—$CH_2CH_2CH_2CH_2$-(4-(3-pyridyl)-1-imidazolyl), $R_1$=H, $R_{P1}$=H, Z=acetyl;     Compound of formula I A=—$CH_2CH_2CH_2CH_2$-(4-(3-pyridyl)-1-imidazolyl), $R_1$=H, $R_{P1}$=H, Z=H;     Compound of formula I A=—$CH_2CH_2CH_2CH_2$-(4-(3-pyridyl)-1-imidazolyl), $R_1$=H, $R_{P1}$=
H, $R_{P2}$=—$CH_2CH$=$CH_2$;   Compound of formula I A=—$CH_2CH$=$CH_2$, $R_1$=H, $R_{P1}$=
H, $R_2$=H;   Compound of formula II A=—$CH_2CHCH_2$, $R_1$=H, $R_2$=—$C(O)CH_2$-
(2-pyridyl), $R_{P1}$=H;   Compound of formula II A=—$CH_2CH_2CH_2$-(3-quinolyl), $R_1$=H, $R_2$=
H and $R_{P1}$=H;   Compound of formula II and A=—$CH_2CH_2CH_2$-(3-quinolyl), $R_1$=H, $R_2$=
H, $R_{P1}$=H.   Compound of formula II

DEFINITIONS

The terms "$C_1$–$C_3$-alkyl" or "$C_1$–$C_6$-alkyl," as used herein, refer to saturated, straight- or branched-chain hydrocarbon radicals containing between one and three or one and six carbon atoms, respectively. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "C2–C6-alkenyl," as used herein, refers to straight- or branched-chain hydrocarbon radicals containing between two and six carbon atoms with one or more double bonds in the chain. Examples of C2–C6-alkenyl include, but are not limited to, propenyl, isobutenyl, 1,3-hexadienyl, n-hexenyl, and 3-pentenyl.

The term "C2–C6-alkynyl," as used herein, refers to straight- or branched-chain hydrocarbon radicals containing between two and six carbon atoms with one or more triple bonds in the chain optionally containing one or more double bond. Examples of C2–C6-alkynyl include, but are not limited to, propynyl, isopentynyl, 1,3-hexadiynyl, n-hexynyl, 3-pentynyl, and 1-hexen-3-ynyl.

The term "aprotic solvent," as used herein, refers to a solvent that is relatively inert to proton activity, i.e., not acting as a proton-donor. Examples include, but are not limited to, hydrocarbons, such as for example, hexane and toluene, and the like, halogenated hydrocarbons, such as, for example, methylene chloride, ethylene chloride, chloroform, and the like, heterocyclic compounds, such as, for example, tetrahydrofuran, N-methylpyrrolidinone, and the like and ethers such as for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl" as used herein refers to unsubstituted carbocyclic aromatic groups including, but not limited to, phenyl, 1- or 2-naphthyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The terms "halo" and "halogen," as used herein, refer to an atom selected from fluorine, chlorine, bromine or iodine.

The term "heterocyclic", as used herein, refers to heterocycloalkyl and heteroaryl. The term "substituted heterocyclic", as used herein, refers to substituted heterocycloalkyl and substituted heteroaryl.

The term "substituted aryl" as used herein refers to an aryl group as defined herein substituted by independent replacement of one or more of the hydrogen atoms therein with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroaryl" as used herein refers to a heteroaryl group as defined herein substituted by independent replacement of one or more of the hydrogen atoms therein with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

"Hydroxy protecting group," as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptalble salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design*, American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 µg/ml to about 0.03 µg/ml. The diluted compounds (2 µl/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 µl/well of adjusted bacterial inoculum. The 96 well plates were covered and incubated at 35+/-2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the schemes and the examples that follow are: BOC for tert-Butoxycarbonyl; BSA for bis(trimethylsilyl)acetamide; DCC for 1,3-dicyclohexylcarbodiimide; DMAP for 4-N,N-dimethylamino-pyridine; DMF for dimethyl formamide; DMSO for dimethylsulfoxide; dppb for 1,4-bis(diphenylphosphino)butane; dppe for 1,2-bis(diphenylphosphino)ethane; EtOAc for ethyl acetate; HMDS for 1,1,1,3,3,3-Hexamethyldisilazane; KHMDS for potassium bis(trimethylsilyl)amide; MeOH for methanol; NMO for N-methylmorpholine N-oxide; TEA for triethylamine; THF for tetrahydrofuran; TPP for triphenylphosphine; TBAF for tetrabutylammonium fluoride; TFA for trifluoroacetic acid; TPAP for tetrapropylammonium perruthenate; Ac for acetyl and Bz for benzoyl.

Synthetic Methods

The compounds and processes of the present invention will be better understood in connection with the following synthetic schemes that are illustrative of the methods by which the compounds of the invention may be prepared. The groups A, $R_1$, $R_2$, $Rp_1$, and Z are as defined previously, unless otherwise noted below.

Scheme 1

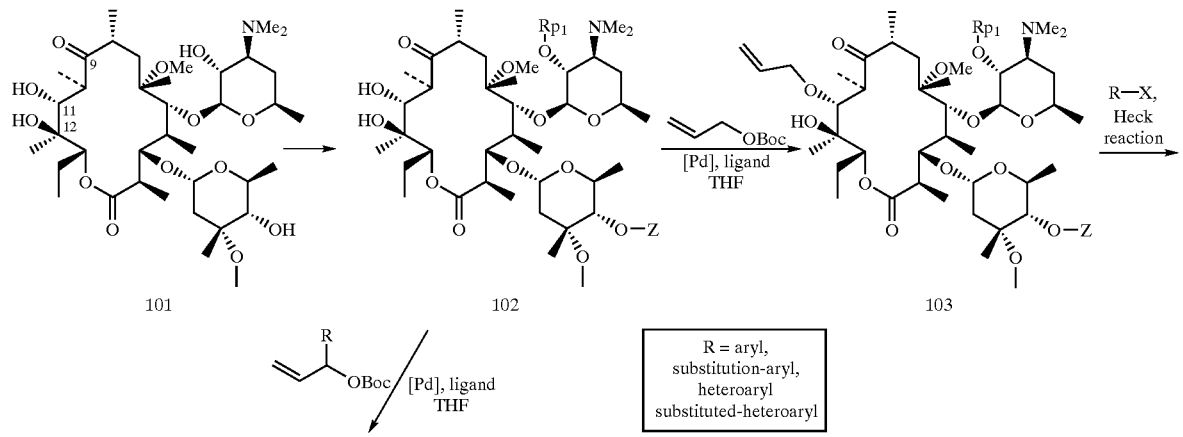

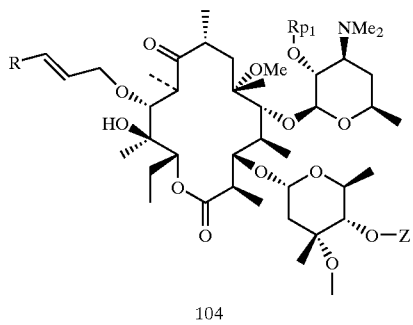

104

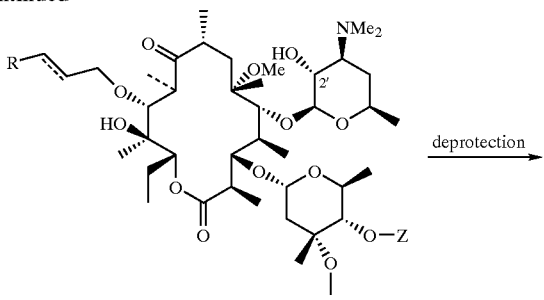

105

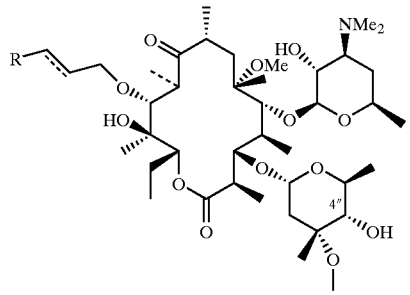

106

One process of the present invention is as shown in Scheme 1. According to this synthetic scheme, the preparation of the compounds of formula I comprises protection of Clarithromycin (compound 101 of Scheme 1) with an acid anhydride or a silylating reagent such as silyl chloride, HMDS, BSA and the like in an aprotic solvent such as methylene chloride, THF, chloroform, DMF, acetonitrile or the like at a temperature from about 0° C. to about 50° C. for 3–72 hours to provide compound 102. Compound 102 is treated with a tert-butyl allyl carbonate catalyzed by a palladium catalyst [Pd(0) or Pd(II)] with a phosphorus ligand such as, for example, dppb, dppe and the like, in aprotic solvents to provide compound 103 from room temperature to about 100° C. (see (a) Trost, B. M. *Angew. Chem. Int. Ed. Eng.* 1989, 28, 1179; (b) Heck, Palladium Reagents in Organic Synthesis, Academic Press: New York, 1985, Chapter 1; (c) Tsuji, *Tetrahedron Lett.* 1992, 33, 2987). Compound 103 further reacts with an aryl halide or aryl triflate in the presence of a palladium catalyst [Pd(0) or Pd(II)] with a phosphorus ligand and a base such as TEA, $K_2CO_3$ and the like, to provide compound 104 (See (a) Heck, Palladium Reagents in Organic Synthesis, Academic Press: New York, 1985, Chapter 1; (b) Sonogashira, Comprehensive Organic Synthesis, Volume 3, Chapters 2,4; (c) Sonogashira, *Synthesis* 1977, 777). Alternatively, compound 104 can be obtained under similar conditions by treating compound 102 with an aryl tert-butyl allyl carbonate catalyzed by a palladium catalyst. Compound 104 is optionally hydrogenated with palladium on carbon, platinum oxide, or the like under 1–4 atm of hydrogen in an organic solvent like methanol, ethanol, ethyl acetate or the like at a temperature from about 0° C. to about 50° C. for 1–36 hours to provide the corresponding saturated linker at C-11 position. Either compound 104 or the reduced form of compound 104 is treated with methanol from 0° C. to 60° C. to remove the acyl protecting group at 2' position to form compound 105. Compound 105 is deprotected to form compound 106. When Z is silyl protecting group, the deprotection process includes, for example, but not limited to, acid hydrolysis with dilute aqueous acid (0.1–2 N) such as hydrochloric acid, sulfuric acid, trifluoroacetic acid, acetic acid and the like, optionally in an organic solvent such as acetone, acetonitrile, methanol, ethanol or the like, or combinations thereof, or TBAF and the like; When Z is an ester protecting group, the deprotection process includes, for example, but not limited to, base hydrolysis by using an alkaline hydroxide aqueous solution, optionally in an organic solvent such as THF, methanol, acetonitrile or the like, at room temperature to 70° C. for 1–24 hours or other like conditions. Compound 106 may be further derivatized at the 4"-hydroxy position as described in Antimicrob. Agents Chemother. 1989, vol 33, page 78–81 or EP 895999, which are herein incorporated by reference in their entirety.

Scheme 2

103

104a

-continued

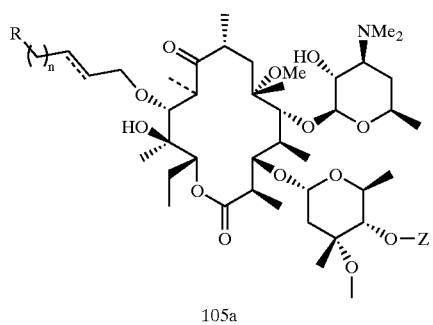

105a

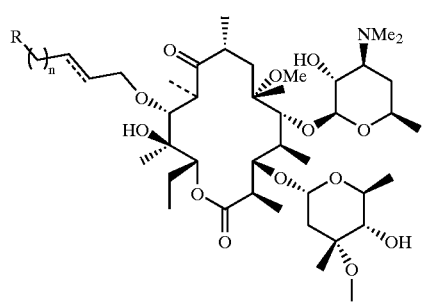

106a

R = aryl,
substitution-aryl,
heteroaryl
substituted-heteroaryl

In another process of the present invention, for the preparation of the compounds of formula I (as shown in Scheme 2), compound 103 of Scheme 1 undergoes a cross metathesis reaction with arylalkene derivatives using ruthenium catalysts in an aprotic solvent such as methylene chloride, THF, chloroform, DMF, acetonitrile, or the like, at a temperature from about 0° C. to about 100° C. for 1–48 hours to produce compound 104a (see (a) *J. Org. Chem.* 2000, 65, 2204–2207; (b) Reviews: *Synlett.* 1999, 2, 267; (c) Reviews: Ivin, K. J.; Mol, J. C. *Olefin Metathesis and Metathesis Polymerization*, 2$^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; (f) *Tetrahedron* 1998, 54, 4413–4450). Compound 104a is optionally hydrogenated as described in Scheme 1 and then is treated with methanol as described in Scheme 1 to form compound 105a. Compound 105a is then deprotected to provide compound 106a as described in Scheme 1.

Scheme 3

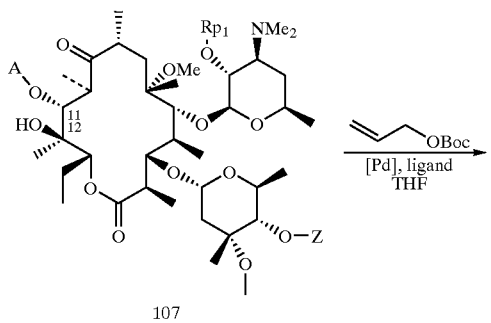

107

-continued

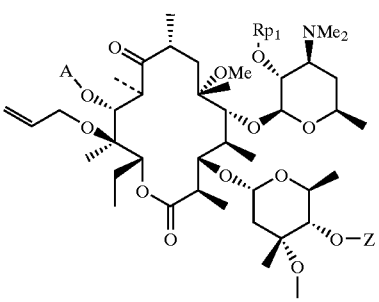

108

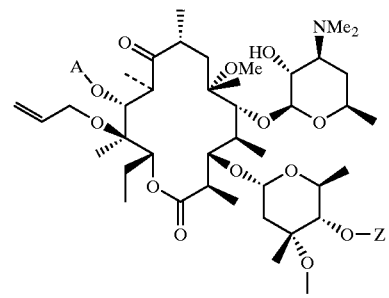

109

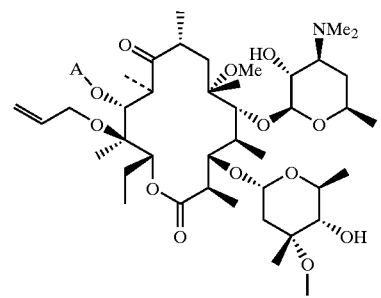

110

In yet another process of the present invention, the preparation of the compounds of formula I, compound 107 undergoes a substitution reaction on the 12-hydroxyl of the macrolide. One of such examples is shown in Scheme 3 with a palladium catalyzed allylation reaction as described in Scheme 1, in addition, the reaction is carried out under slightly forced conditions, for example, for longer time duration (about 30–40 hrs), excess reagents, etc. Then compound 108 is first treated with methanol and followed by the deprotection process to give compound 110, following the procedures described in Scheme 1.

Scheme 4

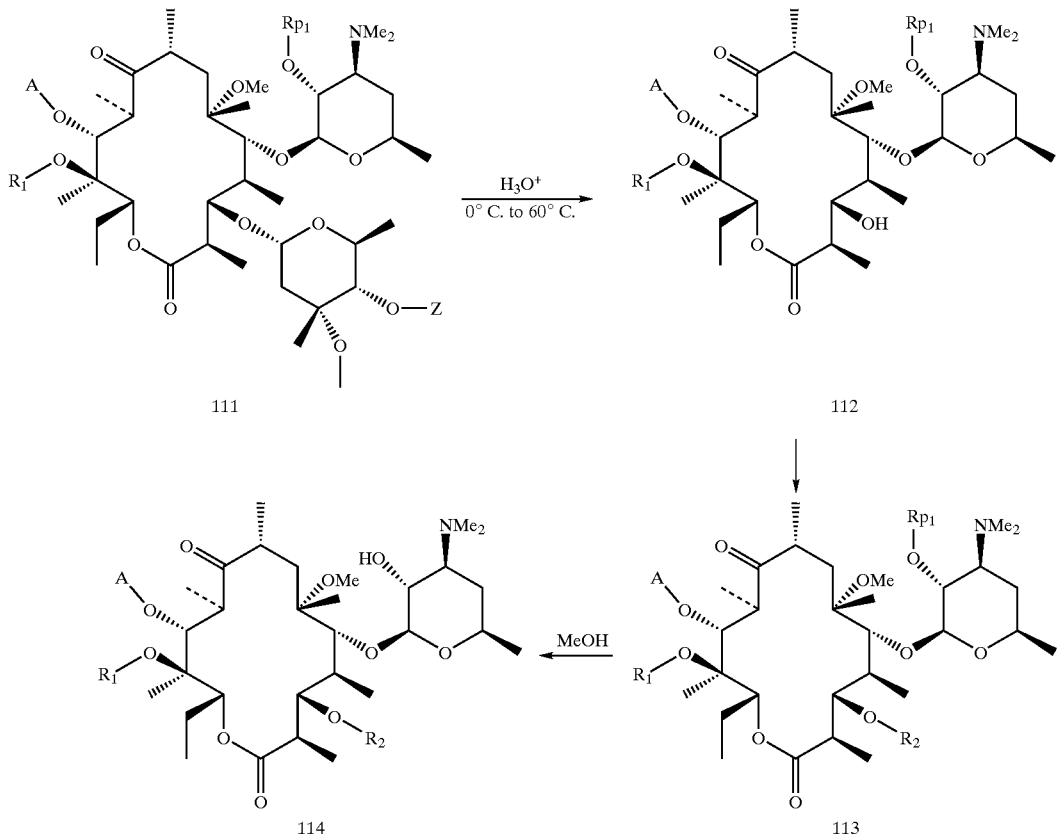

Another process of the present invention involves the preparation of the compounds of formula II (as shown in Scheme 4) that comprises the step of reacting compound 111 with dilute aqueous acid (0.1–2 N) such as hydrochloric acid, sulfuric acid, trifluoroacetic acid, acetic acid and the like, optionally in an organic solvent such as acetone, acetonitrile, methanol, ethanol or the like, or combinations thereof, at a temperature from about 0° C. to about 70° C. for 1–24 hours to provide compound 112. Compound 112 is then either alkylated or acylated to produce compound 113. The alkylating process is either done with palladium catalyzed allylation with tert-butyl allyl carbonate as described in scheme 1, or is done with other alkylating agents, for example, but not limited to, an alkyl halide, alkyl sulphonate, propargyl halide, allyl halide, benzylic halide, or the like, in the presence of a base such as sodium hydride, potassium hydride, potassium tert-butoxide, potassium hydroxide, KHMDS, or the like in an aprotic solvent such as THF, DMSO, DMF, dioxane, or the like or mixtures there of at a temperature from about −20° C. to about 60° C. The acylation process involves the use of a carboxylic acid, its anhydride or mixed anhydride, acid halide or other activated acyl derivatives, optionally with the addition of coupling agent DCC or the like, and optionally with the addition of DMAP and imidazole or the like. Compound 113 can be treated with methanol as described in Scheme 1 to produce compound 114.

EXAMPLES

The procedures described above for preparing the compounds of Formula I of the present invention will be better understood in connection with the following examples which are intended to be illustrative only of, and not limiting of the scope of the invention. Various changes and modifications to the disclosed embodiments will be apparent to those skilled in the art. Such changes and modifications, including without limitation, those relating to the chemical structures, substituents, derivatives, syntheses, formulations and/or methods of the invention may be made without departing from the spirit of the invention and the scope of the appended claims.

Example 1

Compound of Formula I: A=—CH$_2$CH=CH$_2$, R$_1$=H, R$_{P1}$=H, Z=acetyl

Step 1a. Compound of Formula I: A=H, R$_1$=H, R$_{p1}$=Z=acetyl

To a stirring solution of Clarithromycin (3.8 g, 5.0 mmol), acetic anhydride (1.04 mL, 11 mmol), and triethylamine (3.0 mL, 22 mmol) in CH$_2$Cl$_2$ (15 mL), DMAP (20 mg) was added at room temperature. The solution was stirred for 12 h. Then the reaction mixture was diluted with 80 mL ethyl acetate. The resulting solution was washed with water, saturated aqueous NaHCO$_3$ and brine. The organic layer was dried over anhydrous Na$_2$SO$_4$. The solvent was concentrated under vacuum and the residue was purified on a silica gel column (eluting with CH$_2$Cl$_2$ containing 4% 2M ammonia solution in methanol) to provide the title compound (3.7 g, 88% yield) as a white solid.

MS (ESI) m/z 832 (M+H)$^+$.

$^{13}$C-NMR (100 MHz, CDCl$_3$): δ221.3, 175.7, 170.6, 170.1, 100.1, 95.9, 80.3, 78.7, 78.4, 77.8, 76.7, 74.4, 72.9, 72.1, 69.3, 67.4, 63.3(2), 50.7, 49.5, 45.4, 45.0, 40.9, 38.8, 38.7, 37.4, 35.3, 31.3, 21.7, 21.3(2), 21.1, 19.9, 18.5, 18.1, 16.3, 16.1, 14.4, 12.5, 10.7, 9.2.

Step 1b. Compound of Formula I: A=$CH_2CH=CH_2$, $R_1$=H, $R_{P1}$=Z=acetyl

The compound from step 1a (1.2 g, 1.4 mmol) in 30 mL anhydrous THF with $Pd_2(dba)_3$ (60 mg, 0.07 mmol) and dppb (57 mg, 0.14 mmol) was degassed at −78° C. Then the solution was warmed up to room temperature under nitrogen. The allyl t-butyl carbonate (0.44 g, 3.0 mmol) was introduced and the reaction solution was heated to reflux slowly. After 2 hours, the reaction was cooled down and solvent was removed under reduced pressure. The residue was purified by chromatography on a silica gel column (eluting with $CH_2Cl_2$ containing 10% 2M ammonia solution in methanol) to provide the title compound (1.35 g, 100%) as a white solid.

MS (ESI) m/z 872 (M+H)$^+$.

$^{13}$C-NMR (100 MHz, $CDCl_3$): δ217.2, 175.5, 170.6, 170.1, 136.0, 115.8, 99.9, 96.2, 79.4, 79.1, 78.6, 78.1, 77.7, 77.3, 76.2, 73.9, 72.8, 72.2, 67.3, 63.4, 50.6, 49.4, 45.9, 44.9, 40.9, 38.0, 37.8, 37.3, 35.4, 31.3, 21.8, 21.7, 21.3, 21.0, 20.4, 19.5, 18.5, 17.8, 16.2, 13.2, 10.7, 9.3.

Step 1c. Compound of formula I: A=—$CH_2CH=CH_2$, $R_1$=H, $R_{P1}$=H, Z=acetyl

A solution of the compound from step 1b (50 mg) in methanol was refluxed for 4 hours. The solvent was evaporated under vacuum. Purification on silica gel column (eluting with $CH_2Cl_2$ containing 10% 2M ammonia solution in methanol) gave the title compound (40 mg, 84%) as a white solid.

MS (ESI) m/z 830 (M+H)$^+$.

$^{13}$C-NMR (100 MHz, $CDCl_3$): δ217.3, 175.7, 170.7, 136.1, 115.8, 102.0, 96.4, 79.6, 79.2, 78.8, 78.5, 77.7, 77.3, 76.3, 73.9, 72.8, 71.4, 67.9, 65.4, 63.3, 50.8, 49.6, 45.9, 44.9, 40.4, 38.1, 37.8, 35.4, 28.9, 22.0, 21.8, 21.3, 21.1, 20.4, 19.6, 18.6, 17.7, 16.2, 13.2, 10.7, 9.5.

Example 2

Compound of Formula I: A=—$CH_2CH=CH$-(3-quinolyl), $R_1$=H, $R_{P1}$=H, Z=acetyl Step 2a. Compound of Formula I: A=—$CH_2CH=CH$-(3-quinolyl), $R_1$=H, $R_{P1}$=acetyl, Z=acetyl The compound from step 1b (0.1 g, 0.11 mmol), 3-bromoquinoline (35 uL, 0.25 mmol), Pd(OAc)$_2$ (2.5 mg, 0.01 mmol), (o-Tolyl)$_3$P (10 mg, 0.03 mmol) and triethyl amine (0.1 mL, 0.7 mmol) were dissolved in 1 mL $CH_3CN$ and the solution was degassed at −40° C. The reaction mixture was warmed up to RT and sealed under nitrogen, then was heated at 50° C. for 2 h, then at 80° C. for 12 h. The reaction mixture was diluted with ethyl acetate, washed with saturated aqueous NaHCO$_3$, and dried over anhydrous Na$_2$SO$_4$. The solvent was evaporated to give the crude title compound.

MS (ESI) m/z 999 (M+H)$^+$.

Step 2b. Compound of Formula I: A=—$CH_2CH=CH$-(3-quinolyl), $R_1$=H, $R_{P1}$=H, Z=acetyl A solution of the compound from step 2a in methanol (10 mL) was stirred for 16 hours at room temperature. The solvent was evaporated under vacuum. Two silica gel columns were used to purify the title compound (first column: eluting with 10% MeOH in acetone; second column: eluting with 5% triethylamine in acetonitrile). The title compound was obtained as a white solid (60 mg, 50% for 2 steps).

MS (ESI) m/z 957 (M+H)$^+$.

$^{13}$C-NMR (100 MHz, $CDCl_3$): δ217.6, 175.9, 170.7, 149.9, 147.6, 132.6, 130.4, 130.2, 129.4, 129.2, 128.3, 128.2, 128.0, 127.0, 102.0, 96.5, 79.5, 79.3, 78.8, 78.5, 77.4, 76.4, 73.9, 72.8, 71.3, 67.9, 65.4, 63.3, 50.9, 49.6, 45.9, 44.9, 40.4, 38.1, 38.0, 35.4, 29.5, 22.0, 21.3, 21.1, 20.5, 19.6, 18.6, 17.8, 16.2, 13.3, 10.8, 9.5.

Example 3

Compound of Formula I: A=—$CH_2CH_2CH_2$-(3-quinolyl), $R_1$=H, $R_{P1}$=H, Z=acetyl The product from step 2b (10 mg) was hydrogenated under 1 atm H$_2$ over Pd—C in ethanol at room temperature for 3 hours. The solvent was evaporated under vacuum. Purification on silica gel column (eluting with $CH_2Cl_2$ containing 10% methanol) gave the title compound (7.5 mg, 75%) as a white solid.

MS (ESI) m/z 959 (M+H)$^+$.

Example 4

Compound of Formula I: A=—$CH_2CH=CH$-(3-quinolyl), $R_1$=H, $R_{P1}$=H, Z=H

Step 4a. Compound of Formula I: A=H, $R_1$=H, $R_{P1}$=TMS, Z=TMS

Clarithromycin (3.8 g, 5.0 mmol) and HMDS (3.2 mL, 15 mmol) were dissolved in 30 mL $CH_3CN$ and 20 mL $CH_2Cl_2$. After stirred for 60 hours, 1.0 mL HMDS (5.0 mmol) was added and the solution was stirred for another 12 hours. The crude title compound (4.6 g, 100%, as white solid) was obtained by removing the solvent and excess HMDS under vacuum.

MS (ESI) m/z 892 (M+H)$^+$.

Step 4b. Compound of Formula I: A=—$CH_2CH=CH$-(3-quinolyl), $R_1$=H, $R_{P1}$=H, Z=H The product from step 4a (0.45 g, 0.5 mmol) in 20 mL anhydrous THF was processed as described in step 1b, substituting 1-quinolyl-allyl t-butyl carbonate (2.5 equiv.) for allyl t-butyl carbonate. After 1.5 hours, 10 mL of 1 N HCl aqueous solution was added and the resulting mixture was stirred for 10 minutes at room temperature. Saturated aqueous NaHCO$_3$ (20 mL) was added and the aqueous layer was extracted 3 times with ethyl acetate. The combined organic layer was dried over anhydrous Na$_2$SO$_4$. The solvent was concentrated under vacuum and the residue was purified on a silica gel column (eluting with $CH_2Cl_2$ containing 3% 2M ammonia solution in methanol) to provide the title compound (0.42 g, 91%) as a white solid.

MS (ESI) m/z 915 (M+H)$^+$.

$^{13}$C-NMR (100 MHz, $CDCl_3$): δ217.7, 176.0, 149.8, 147.5, 132.6, 130.3, 130.2, 129.3, 129.2, 128.3, 128.2, 128.0, 127.0, 102.7, 96.5, 79.9, 79.3, 78.8, 78.1, 76.3, 73.3, 72.9, 71.2, 68.8, 66.0, 65.7, 50.9, 49.6, 45.9, 45.1, 40.4, 38.2, 38.1, 38.0, 35.2, 28.7, 21.7, 21.6, 20.6, 19.5, 18.9, 17.9, 16.2, 13.2, 10.8, 9.4.

Example 5

Compound of Formula I: A=$R_1$=—$CH_2CH=CH_2$, $R_{P1}$=H, Z=acetyl

Step 5a. Compound of Formula I: A=$R_1$=—$CH_2CH=CH_2$, $R_{P1}$=acetyl, Z=acetyl The product from step 1a (1.67 g, 2 mmol) in 15 mL anhydrous THF and allyl t-butyl carbonate (1.26 g, 8.0 mmol) was processed as described in step 1b. After 24 hours at reflux, the solvent was evaporated under vacuum and the residue was purified on silica gel column (eluting with $CH_2Cl_2$ containing 4% 2M ammonia solution in methanol) to provide the title compound (1.5 g, 79%) as a white solid.

MS (ESI) m/z 912 (M+H)$^+$.

Step 5b. Compound of Formula I: A=$R_1$=—$CH_2CH=CH_2$, $R_{P1}$=H, Z=acetyl

The compound from step 5a (100 mg, 0.11 mmol) in methanol (10 mL) was refluxed for 2 hours. The solvent was removed under vacuum and the residue was purified on silica gel column (eluting with $CH_3CN$ containing 3% triethylamine) to provide the title compound (14 mg, 15%) as a white solid.

MS (ESI) m/z 870 (M+H)$^+$.

$^{13}$C-NMR (100 MHz, CDCl$_3$): δ217.9, 175.0, 170.7, 136.6, 136.3, 115.3, 114.7, 102.1, 96.6, 81.0, 79.9, 79.4, 79.3, 78.8, 78.7, 77.4, 76.3, 75.5, 73.8, 72.8, 71.4, 67.8, 66.9, 65.4, 63.3, 50.7, 49.6, 44.8, 44.6, 40.4, 40.0, 35.5, 29.9, 22.0, 21.9, 21.3, 21.1, 20.7, 20.1, 19.8, 18.6, 16.1, 12.6, 10.7, 9.7.

Example 6

Compound of Formula I: A=—$CH_2CH$=$CHCH_2$-(4-phenyl-1-imidazolyl), $R_1$=H, $R_{P1}$=H, Z=acetyl Step 6a. 1-allyl-4-phenylimidazole To a solution of 4-Phenylimidazole (2.0 g, 13.9 mmol) in 20 mL DMF was added NaH (60% in mineral oil, 0.7 g, 17.4 mmol) at 0° C. After stirring for 10 minutes, allyl bromide (3.5 mL, 41.4 mmol) was added through a syringe. The reaction was stirred for 12 hours at RT, the solvent was evaporated under vacuum and the residue was purified on silica gel column (eluting with ethyl acetate) to provide the title compound (2.2 g, 88%) as a light yellow liquid.

MS (ESI) m/z 185 (M+H)$^+$.

$^1$H-NMR (400 MHz, CDCl$_3$): δ7.73 (2H, d), 7.48 (1H, s), 7.33 (2H, t), 7.22–7.15 (3H, m), 6.00–5.90 (1H, m), 5.28–5.18 (2H, m), 4.53–4.51 (2H, m).

Step 6b. Compound of Formula I: A=—$CH_2CH$=$CHCH_2$-(4-phenyl-1-imidazolyl), $R_1$=H, $R_{P1}$=acetyl, Z=acetyl To a solution of the compound from step 6a (80 mg, 0.4 mmol) and the compound from step 1b (0.38 g, 0.4 mmol) in $CH_2Cl_2$ (15 mL) was added Bis(tricyclohexylphosphino)-3-methyl-2-Buten-ylidene ruthenium (IV) dichloride (64 mg, 0.08 mmol). The solution as refluxed for 16 hours. The solvent was removed under vacuum and the residue was purified on silica gel column (eluting with acetone:hexanes/3:2) to provide the title compound (0.18 g, 40%) as a white solid.

MS (ESI) m/z 1028 (M+H)$^+$.

Step 6c. Compound of Formula I: A=—$CH_2CH$=$CHCH_2$-(4-phenyl-1-imidazolyl), $R_1$=H, $R_{P1}$=H, Z=acetyl The compound from step 6b (25 mg, 0.025 mmol) in methanol (10 mL) was refluxed for 3 hours. The solvent was removed under vacuum and the residue was purified on silica gel column (eluting with acetone) to provide the title compound (20 mg, 83%) as a white solid.

MS (ESI) m/z 986 (M+H)$^+$.

Selected $^{13}$C-NMR (100 MHz, CDCl$_3$): δ217.4, 175.8, 170.7, 142.3, 137.4, 134.5, 132.9, 128.7, 126.8, 125.6, 125.0, 115.1, 101.9, 96.4.

Example 7

Compound of Formula I: A=—$CH_2CH_2CH_2CH_2$-(4-phenyl-1-imidazolyl), $R_1$=H, $R_{P1}$=H, Z=acetyl Step 7a. Compound of Formula I: A=—$CH_2CH_2CH_2CH_2$-(4-phenyl-1-imidazolyl), $R_1$=H, $R_{P1}$=acetyl, Z=acetyl The product from step 6b (140 mg) was hydrogenated under 1 atm $H_2$ over Pd—C in ethanol for 16 hours. The solvent was evaporated under vacuum. Purification on silica gel column (eluting with ethyl actate to ethyl actate with 5% triethylamine) gave the title compound (110 mg, 79%) as a white solid.

MS (ESI) m/z 1030 (M+H)$^+$.

$^{13}$C-NMR (100 MHz, CDCl$_3$): δ217.7, 175.6, 170.5, 170.1, 142.2, 137.6, 134.6, 128.6, 126.6, 124.9, 115.0, 99.8, 96.2, 79.3, 79.1, 78.6, 78.1, 77.6, 76.4, 76.2, 72.8, 72.2, 70.9, 67.3, 63.39, 63.36, 60.5, 50.6, 49.4, 46.8, 46.0, 44.8, 40.9, 37.9, 37.8, 37.2, 35.4, 31.2, 27.6, 27.2, 21.7, 21.2, 21.0, 20.4, 19.5, 18.5, 14.3, 13.2, 10.7, 9.3.

Step 7b. Compound of Formula I: A=—$CH_2CH_2CH_2CH_2$-(4-phenyl-1-imidazolyl), $R_1$=H, $R_{P1}$=H, Z=acetyl The product from step 7a (25 mg) was processed as described in steps 6c to provide the title compound (18 mg, 75%) as a white solid.

MS (ESI) m/z 988 (M+H)$^+$.

$^{13}$C-NMR (100 MHz, CDCl$_3$): δ217.8, 175.8, 170.6, 142.3, 137.6, 134.6, 128.7, 126.7, 124.9, 115.0, 101.9, 96.4, 79.5, 79.2, 78.8, 78.4, 77.6, 76.5, 76.3, 72.8, 71.4, 70.9, 67.8, 65.4, 63.3, 50.8, 49.6, 46.9, 46.1, 44.9, 40.5, 38.1, 38.0, 37.8, 35.4, 27.7, 27.3, 22.0, 21.8, 21.3, 21.1, 20.4, 19.6, 18.6, 17.6, 16.2, 13.3, 10.8, 9.5.

Example 8

Compound of Formula I: A=—$CH_2CH_2CH_2CH_2$-(4-phenyl-1-imidazolyl), $R_1$=H, $R_{P1}$=H, Z=H To a solution of the compound from step 7b (15 mg, 0.015 mmol) in THF (1 mL) and distilled water (1 mL) was added 1N LiOH (0.1 mL, 0.10 mmol). The mixture was stirred 2 hours at RT, then 3 hours at 50° C. Then 10 mL water was added and extracted with ethyl actate. The combined organic layer was dried over anhydrous $Na_2SO_4$. The solvent was concentrated under vacuum and the residue was purified on a silica gel column (eluting with $CH_2Cl_2$ containing 20% methanol) to provide the title compound (9.0 mg, 63%) as a white solid.

MS (ESI) m/z 946 (M+H)$^+$.

Selected $^{13}$C-NMR (100 MHz, CDCl$_3$): δ217.7, 175.9, 142.3, 137.6, 134.6, 128.7, 126.7, 124.9, 115.0, 102.4, 96.5.

Example 9

Compound of Formula I: A=—$CH_2CH_2CH_2CH_2$-(4-(3-pyridyl)-1-imidazolyl), $R_1$=H, $R_{P1}$=H, Z=acetyl Step 9a. 1-Allyl-4-(3-pyridyl)-imidazole The title compound is prepared according to the procedure of Step 6a by substituting 4-Phenylimidazole with 4-(3-Pyridyl)-imidazole.

Step 9b. Compound of Formula I: A=—$CH_2CH$=$CHCH_2$-(4-(3-pyridyl)-1-imidazolyl), $R_1$=H, $R_{P1}$=acetyl, Z=acetyl Compounds of step 1b and step 9a are treated according to the procedure of step 6b to provide the title compound.

Step 9c. Compound of Formula I: A=—$CH_2CH_2CH_2CH_2$-(4-(3-pyridyl)-1-imidazolyl), $R_1$=H, $R_{P1}$=acetyl, Z=acetyl The compound from step 9b is processed as described in step 7a to provide the title compound.

Step 9d. Compound of Formula I: A=—$CH_2CH_2CH_2CH_2$-(4-(3-pyridyl)-1-imidazolyl), $R_1$=H, $R_{P1}$=H, Z=acetyl The product from step 9c is processed as described in step 6c to provide the title compound.

Example 10

Compound of Formula I: A=—$CH_2CH_2CH_2CH_2$-(4-(3-pyridyl)-1-imidazolyl), $R_1$=H, $R_{P1}$=H, Z=H The compound from step 9d is converted to the title compound following the procedure described in Example 8.

Example 11

Compound of Formula I: A=—$CH_2CH_2CH_2CH_2$-(4-(3-pyridyl)-1-imidazolyl), $R_1$=H, $R_{P1}$=H, Z=—$CH_2CHCH_2$ Step 11a. Compound of Formula I: A=—$CH_2CH_2CH_2CH_2$-(4-(3-pyridyl)-1-imidazolyl), $R_1$=H, $R_{P1}$=Acetyl, Z=—$CH_2CHCH_2$ The compound from example 10 is treated with acetic anhydride (1.2 equivalent) in $CH_2Cl_2$ at room temperature. The solution is stirred for 12 hours. Then the reaction mixture is diluted with ethyl acetate. The resulting solution is washed with water, saturated aqueous $NaHCO_3$ and brine. The organic layer is dried over anhydrous $Na_2SO_4$ and the solvent is concentrated under vacuum. The resulting crude residue is subjected to the allylation condition as described in step 1b. The residue is purified by chromatography on a silica gel column (eluting with acetone:hexanes/2:1) to provide the title compound.

Step 11b. Compound of Formula I: A=—CH$_2$CH$_2$CH$_2$CH$_2$-(4-(3-pyridyl)-1-imidazolyl), R$_1$H, R$_{P1}$=H, Z=—CH$_2$CHCH$_2$ The compound from step 11a is treated with methanol as described in step 1c to provide the title compound.

Example 12
Compound of Formula II: A=—CH$_2$CHCH$_2$, R$_1$=H, R$_{P1}$=H, R$_2$=H Step 12a. Compound of Formula II: A=—CH$_2$CHCH$_2$, R$_1$=H, R$_{P1}$=acetyl, R$_2$=H The compound from step 1b (100 mg, 0.11 mmol) in ethanol (2 mL) and 0.5 mL HCl (4 mL) was heated at 65° C. for 1 hour. Then 10 ml of saturated aqueous NaHCO$_3$ was added and the aqueous layer was extracted 3 times with CH$_2$Cl$_2$. The combined organic layer was dried over anhydrous Na$_2$SO$_4$. The solvent was concentrated under vacuum and the residue was purified on a silica gel column (eluting with CH$_2$Cl$_2$ containing 4% 2M ammonia solution in methanol) to provide the title compound (50 mg, 65%) as a white solid.

MS (ESI) m/z 672 (M+H)$^+$.

$^{13}$C-NMR (100 MHz, CDCl$_3$): δ216.9, 175.0, 170.1, 135.8, 116.1, 100.0, 80.0, 79.0, 77.9, 77.7, 76.2, 74.2, 71.7, 69.0, 63.4, 49.9, 46.2, 44.3, 40.9, 37.9, 37.4, 36.2, 31.2, 22.0, 21.7, 21.3, 19.8, 19.4, 17.8, 15.3, 13.3, 10.7, 8.1.

Step 12b. Compound of Formula II: A=—CH$_2$CHCH$_2$, R$_1$=H, R$_{P1}$=H, R$_2$=H A solution of the compound from step 12a (15 mg, 0.02 mmol) in methanol (10 mL) was stirred for 2 hours at 65° C. The solvent was evaporated under vacuum to give the title compound (12 mg, 86%) as a white solid.

MS (ESI) m/z 630 (M+H)$^+$.

$^{13}$C-NMR (100 MHz, CDCl$_3$): δ216.6, 175.5, 135.8, 116.2, 107.0, 79.1, 78.9, 77.4, 76.2, 74.2, 70.8, 70.5, 65.9, 49.7, 46.1, 44.8, 40.5, 38.1, 37.7, 36.2, 28.2, 22.1, 21.5, 19.4, 19.1, 15.3, 13.2, 10.7, 8.5.

Example 13
Compound of Formula II: A=—CH$_2$CH=CH$_2$, R$_1$=H, R$_2$=—C(O)CH$_2$-(2-pyridyl), R$_{P1}$=H Step 13a. Compound of Formula II: A=—CH$_2$CHCH$_2$, R$_1$=H, R$_2$=—C(O)CH$_2$-(2-pyridyl), R$_{P1}$=acetyl The compound from step 12a is treated with Phenylacetic acid and DCC in CH$_2$Cl$_2$ in the presence of 1.5 eqivalents DMAP for 20 hours to produce the title compound.

Step 13b. Compound of Formula II: A=—CH$_2$CHCH$_2$, R$_1$=H, R$_2$=—C(O)CH$_2$-(2-pyridyl), R$_{P1}$=H The compound from step 13a is processed as described in step 1c to provide the title compound.

Example 14
Compound of Formula I: A=—CH$_2$CH$_2$CH$_2$-(3-quinolyl), R$_1$=H, R$_{p1}$=H, Z=H A solution of the compound from step 4b (0.20 g, 0.22 mmol) in EtOH was hydrogenated over Pd/C as described in example 3 for 18 hours. The solvent was concentrated under vacuum and the residue was purified on a silica gel column (eluting with CH$_2$Cl$_2$ containing 4% 2M ammonia solution in methanol) to provide the title compound (170 mg, 85%) as a white solid.

MS (ESI) m/z 917 (M+H)$^+$.

Example 15
Compound of Formula II: A=—CH$_2$CH$_2$CH$_2$-(3-quinolyl), R$_1$=H, R$_2$=H, R$_{P1}$=H The compound from step 14a (170 mg, 0.18 mmol) in MeOH (2 mL) and 0.3N HCl (6 mL) was stirred for 12 hours at room temperature, diluted with saturated aqueous NaHCO$_3$ and extracted with dichloromethane. The solvent was evaporated under vacuum. Purification on silica gel column (eluting with CH$_2$Cl$_2$ containing 4% 2M ammonia solution in methanol) gave the title compound (100 mg, 73%) as a white solid.

MS (ESI) m/z 759 (M+H)$^+$.

$^{13}$C-NMR (100 MHz, CDCl$_3$): δ216.8, 175.5, 152.3, 146.9, 135.3, 134.3, 129.3, 128.6, 128.4, 127.6, 126.6, 106.8, 87.2, 79.1, 78.7, 77.8, 77.4, 76.2, 72.4, 70.8, 70.4, 65.9, 49.6, 46.1, 44.8, 40.4, 38.2, 37.7, 36.4, 31.9, 30.2, 28.2, 22.1, 21.4, 19.4, 19.1, 17.8, 15.3, 13.3, 10.7, 8.5.

Example 16
Compound of Formula I: A=—CH$_2$CH=CHCH$_2$CH$_2$-(4-phenyl-1-imidazolyl), R$_1$=R$_{p1}$=H, Z=acetyl Step 16a. 1-(3-Butenyl)-4-phenylimidazole To a solution of 4-Phenylimidazole (1.45 g, 10.0 mmol) in 10 mL DMF was added NaH (60% in mineral oil, 0.5 g, 12.5 mmol) at 0° C. After the reaction mixture was stirred for 10 minutes, 3-butenyl bromide (2.7 g, 20.0 mmol) was added through a syringe. The reaction was stirred for 12 hours at room temperature, the solvent was evaporated under vacuum and the residue was purified on silica gel column (eluting with ethyl acetate) to provide the title compound (1.4 g, 70%).

MS (ESI) m/z 199 (M+H)$^+$.

Step 16b. Compound of Formula I: A=—CH$_2$CH=CHCH$_2$CH$_2$-(4-phenyl-1-imidazolyl), R$_1$=H, R$_{p1}$=Z=acetyl To a solution of the compound from step 16a (0.14 g, 0.7 mmol) and the compound from step 1b (0.25 g, 0.29 mmol) in CH$_2$Cl$_2$ (15 mL) was added bis-(tricyclohexylphosphino) benzylidine ruthenium (IV) dichloride (50 mg, 0.06 mmol). The solution was refluxed for 16 hours. The solvent was removed under vacuum and the residue was purified on a silica gel column (eluting with acetone:hexanes/1:1) to provide the title compound (0.22 g, 72%).

MS (ESI) m/z 1042 (M+H)$^+$.

Step 16c. Compound of Formula I: A=—CH$_2$CH=CHCH$_2$CH$_2$-(4-phenyl-1-imidazolyl), R$_1$=R$_{p1}$=H, Z=acetyl The compound from step 16b was converted to the title compound following the procedure described in step 6c.

MS (ESI) m/z 1000 (M+H)$^+$.

Example 17
Compound of Formula I: A=—CH$_2$CH$_2$CH$_2$CH$_2$-(4-phenyl-1-imidazolyl), R$_1$=—CH$_2$CH=CH$_2$, R$_{p1}$=H, Z=acetyl Step 17a. Compound of Formula I: A=—CH$_2$CH$_2$CH$_2$CH$_2$-(4-phenyl-1-imidazolyl), R$_1$=—CH$_2$CH=CH$_2$, R$_{p1}$=Z=acetyl The product from step 7a (200 mg, 0.19 mmol), Pd$_2$(dba)$_3$ (20 mg, 0.02 mmol) and dppb (18 mg, 0.04 mmol) were dissolved in 15 mL anhydrous THF. The resulting solution was degassed at −78° C. and warmed up to room temperature under nitrogen and allyl t-butyl carbonate reagent (1.0 mL, excess) was introduced. The reaction mixture was heated for 48 hours before the reaction was cooled down. The solvent was removed under reduced pressure. The residue was purified by chromatography on a silica gel column (eluting with acetone:hexanes/70:30) to provide the title compound (0.12 g, 48%).

MS (ESI) m/z 1070 (M+H)$^+$.

Step 17b. Compound of Formula I: A=—CH$_2$CH$_2$CH$_2$CH$_2$-(4-phenyl-1-imidazolyl), R$_1$=—CH$_2$CH=CH$_2$, R$_{p1}$=H, Z=acetyl The compound from step 17a is treated with MeOH, following the procedure described in step 6c, to provide the title compound.

Example 18

Compound of Formula I: A=—CH$_2$CH$_2$CH$_2$CH$_2$CH$_2$-(4-phenyl-1-imidazolyl), R$_1$=—CH$_2$CH=CH$_2$, R$_{p1}$=H, Z=acetyl Step 18a. Compound of Formula I: A=—CH$_2$CH=CHCH$_2$CH$_2$-(4-phenyl-1-imidazolyl), R$_1$=H, R$_{p1}$=Z=acetyl The product from step 16b (140 mg) was hydrogenated under 1.5 atm H$_2$ over Pd—C in ethanol for 16 hours at room temperature. The solvent was evaporated under vacuum. Purification on silica gel column (eluting with acetone:hexanes/3:2) gave the title compound (130 mg, 93%).

MS (ESI) m/z 1044 (M+H)$^+$.

Step 18b. Compound of Formula I: A=—CH$_2$CH$_2$CH$_2$CH$_2$CH$_2$-(4-phenyl-1-imidazolyl), R$_1$=—CH$_2$CH=CH$_2$, R$_{p1}$=Z=acetyl The compound from step 18a (120 mg, 0.11 mmol) with Pd$_2$(dba)$_3$ (30 mg, 0.03 mmol) and dppb (27 mg, 0.06 mmol) were dissolved in 12 mL anhydrous THF, the solution was degassed at −78° C. The solution was warmed up to room temperature under nitrogen and allyl t-butyl carbonate reagent (1.0 mL, excess) was introduced. The reaction mixture was heated for 48 hours before the reaction was cooled down. The solvent was removed under reduced pressure. The residue was purified by chromatography on a silica gel column (eluting with acetone:hexanes/60:40) to provide the title compound (0.07 g, 55%).

MS (ESI) m/z 1084 (M+H)$^+$.

Step 18c. Compound of Formula I: A=—CH$_2$CH$_2$CH$_2$CH$_2$CH$_2$-(4-phenyl-1-imidazolyl), R$_1$=—CH$_2$CH=CH$_2$, R$_{p1}$=H, Z=acetyl The compound from step 18b is treated with MeOH following the procedure described in step 6c to provide the title compound.

What is claimed is:

1. A compound represented by formula (I) or a pharmaceutical ester, salt or prodrug thereof:

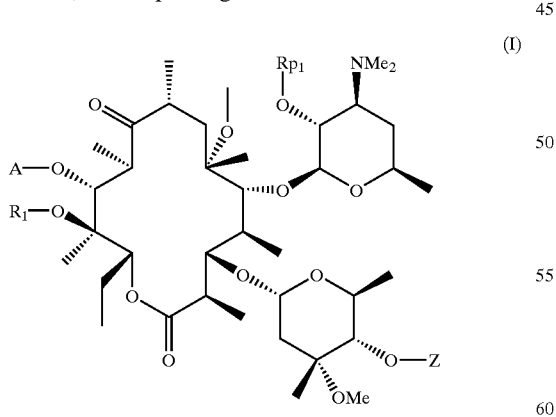

(I)

A is selected from the group consisting of:
(1) C$_1$–C$_6$-alkyl, C$_2$–C$_6$-alkenyl or C$_2$–C$_6$-alkynyl, optionally substituted with one or more substituents selected from the group consisting of:
  i. halogen;
  ii. aryl;
  iii. substituted aryl;
  iv. heteroaryl;
  v. substituted heteroaryl;
  vi. —O—R$_5$, where R$_5$ is selected from the group consisting of:
    a. hydrogen;
    b. aryl;
    c. substituted aryl;
    d. heteroaryl; and
    e. substituted hereroaryl; and
  vii. —O—C$_1$–C$_6$-alkyl-R$_5$, where R$_5$ is as previously defined;
  viii. —O—C$_2$–C$_6$-alkenyl-R$_5$, where R$_5$ is as previously defined;
  ix. —O—C$_2$–C$_6$-alkynyl-R$_5$, where R$_5$ is as previously defined; and
  x. —NR$_6$R$_7$, where R$_6$ and R$_7$ are each independenly selected from hydrogen, C$_1$–C$_6$-alkyl, optionally substituted with one or more substituents selected from the group consisting of halogen, aryl, substituted aryl, heterocyclic and substituted heterocyclic, C$_2$–C$_6$-alkenyl, optionally substituted with one or more substituents selected from the group consisting of halogen, aryl, substituted aryl, heterocyclic and substituted heterocyclic, C$_2$–C$_6$-alkynyl, optionally substituted with one or more substituents selected from the group consisting of halogen, aryl, substituted aryl, hererocyclic and substituted heterocyclic or R$_6$R$_7$ taken with the nitrogen atom to which they are connected form a 3- to 7-membered ring which may optionally contain one or more hetero functions selected from the group consisting of —O—, —NH—, —N(C$_1$–C$_6$-alkyl)-, —N(aryl)-, —N(heteroaryl)-, —S—, —S(O)— and —S(O)$_2$—;
(2) —C(O)—R$_5$, where R$_5$ is as previously defined;
(3) —C(O)—C$_1$–C$_6$-alkyl-R$_5$, where R$_5$ is as previously defined;
(4) —C(O)—C$_2$–C$_6$-alkenyl-R$_5$, where R$_5$ is as previously defined;
(5) —C(O)—C$_2$–C$_6$-alkynyl-R$_5$, where R$_5$ is as previously defined;
(6) —C$_1$–C$_6$-alkyl-M—R$_5$, where M=—OC(O)—, —OC(O)O—, —O C(O)NR$_6$—, —NR$_6$C(O)—, —NR$_6$C(O)O—, —NR$_6$C(O)NR7-, —NR$_6$C(N)NR7-, S(O)$_n$—, where n=0, 1 or 2, and where R$_5$, R$_6$, R$_7$ are as previously defined;
(7) —C$_2$–C$_6$-alkenyl-M—R$_5$, where M=—OC(O)—, —OC(O)O—, —O C(O)NR$_6$—, —NR$_6$C(O)—, —NR$_6$C(O)O—, —NR$_6$C(O)NR7-, —NR$_6$C(N)NR7-, S(O)$_n$—, where n=0, 1 or 2, and where R$_5$R$_6$, R$_7$ are as previously defined; and
(8) —C$_2$–C$_6$-alkynyl-M—R$_5$, where M=—OC(O)—, —OC(O)O—, —O C(O)NR$_6$—, —NR$_6$C(O)—, —NR$_6$C(O)O—, —NR$_6$C(O)NR7-, —NR$_6$C(N)NR7-, S(O)$_n$—, where n=0, 1 or 2, and where R$_5$, R$_6$, R$_7$ are as previously defined;

R$_1$ is selected from the group consisting of:
(1) R$_3$, where R$_3$ is C$_1$–C$_6$-alkyl, C$_2$–C$_6$-alkenyl or C$_2$–C$_6$-alkynyl, optionally substituted with one or more substituents selected from the group consisting of:
  a. halogen;
  b. aryl;
  c. substituted aryl;
  d. heteroaryl;
  e. substituted heteroaryl;

f. —O—$C_1$–$C_6$-alkyl-$R_5$, where $R_5$ is as previously defined; and g. —$NR_6R_7$, where $R_6$ and $R_7$ are as previously defined;

(2) —C(=O)—$R_4$, where $R_4$ is H or $R_3$, where $R_3$ is as previously defined;

(3) —C(=O)O—$R_3$, where $R_3$ is as previously defined; and (4) —C(=O)N—$R_6R_7$, where $R_6$ and $R_7$ are as previously defined;

$Rp_1$ is hydrogen or hydroxy protecting group; and

Z is selected from the group consisting of:
(1) hydrogen;
(2) hydroxy protecting groups; and
(3) —X—$R_3$, where X=—C(O)—, —C(O)O—, —C(O)NH—, or absent, and $R_3$ is as previously defined.

2. A compound represented by formula (II) or a pharmaceutical ester, salt or prodrug thereof:

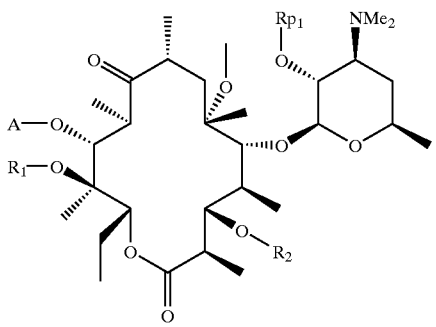

(II)

A is selected from the group consisting of:
(1) $C_1$–$C_6$-alkyl, $C_2$–$C_6$-alkenyl or $C_2$–$C_6$-alkynyl optionally substituted with one or more substituents selected from the group consisting of:
i. halogen;
ii. aryl;
iii. substituted aryl;
iv. heteroaryl;
v. substituted heteroaryl;
vi. —O—$R_5$, where $R_5$ is selected from the group consisting of:
a. hydrogen;
b. aryl;
c. substituted aryl;
d. heteroaryl; and
e. substituted heteroaryl;
vii. —O—$C_1$–$C_6$-alkyl-$R_5$, where $R_5$ is as previously defined;
viii. —O—$C_2$–$C_6$-alkenyl-$R_5$, where $R_5$ is as previously defined;
ix. —O—$C_2$–$C_6$-alkynyl-$R_5$, where $R_5$ is as previously defined; and
x. —$NR_6R_7$, where $R_6$ and $R_7$ are each independently selected from hydrogen, $C_1$–$C_6$-alkyl, optionally substituted with one or more substituents selected from the group consisting of halogen, aryl, substituted aryl, heterocyclic and substituted heterocyclic, $C_2$–$C_6$-alkenyl, optionally substituted with one or more substituents selected from the group consisting of halogen, aryl, substituted aryl, heterocyclic and substituted heterocyclic, $C_2$–$C_6$-alkynyl, optionally substituted with one or more substituents selected from the group consisting of halogen, aryl, substituted aryl, heterocyclic and substituted heterocyclic or $R_6R_7$ taken with the nitrogen atom to which they are connected form a 3- to 7-membered ring which may optionally contain one or more hetero functions selected from the group consisting of —O—, —NH—, —N($C_1$–$C_6$-alkyl)-, —N(aryl)-, —N(heteroaryl)-, —S—, —S(O)— and —S(O)$_2$-;

(2) —C(O)—$R_5$, where $R_5$ is as previously defined;
(3) —C(O)—$C_1$–$C_6$-alkyl-$R_5$, where $R_5$ is as previously defined;
(4) —C(O)—$C_2$–$C_6$-alkenyl-$R_5$, where $R_5$ is as previously defined;
(5) —C(O)—$C_2$–$C_6$-alkynyl-$R_5$, where $R_5$ is as previously defined;
(6) —$C_1$–$C_6$-alkyl-M—$R_5$, where M=—OC(O)—, —OC(O)O—, —O C(O)$NR_6$—, —$NR_6$C(O)—, —$NR_6$C(O)O—, —$NR_6$C(O)NR7-, $NR_6$C(N)NR7-, S(O)$_n$—, where n=0, 1 or 2, and where $R_5$, $R_6$, $R_7$ are as previously defined;
(7) —$C_2$–$C_6$-alkenyl-M—$R_5$, where M=—OC(O)—, —OC(O)O—, —O C(O)$NR_6$-, —$NR_6$C(O)—, —$NR_6$C(O)O—, —$NR_6$C(O)NR7-, $NR_6$C(N)NR7-, S(O)$_n$—, where n=0, 1 or 2, and where $R_5$, $R_6$, $R_7$ are a previously defined; and
(8) —$C_2$–$C_6$-alkynyl-M—$R_5$, where M=—OC(O)—, —OC(O)O—, —O C(O)$NR_6$-, —$NR_6$C(O)—, —$NR_6$C(O)O—, —$NR_6$C(O)NR7-, $NR_6$C(N)NR7-, S(O)$_n$-, where n=0, 1 or 2, and where $R_5$, $R_6$, $R_7$ are as previously defined;

$R_1$ is selected from the group consisting of:
(1) hydrogen;
(2) $R_3$, where $R_3$ is $C_1$–$C_6$-alkyl, $C_2$–$C_6$-alkenyl or $C_2$–$C_6$-alkynyl, optionally substituted with one or more substituents selected from the group consisting of:
a. halogen;
b. aryl;
c. substituted aryl;
d. heteroaryl;
e. substituted heteroaryl;
f. —O—$C_1$–$C_6$-alkyl-$R_5$, where $R_5$ is as previously defined; and
g. —$NR_6R_7$, where $R_6$ and $R_7$ are as previously defined;
(3) —C(=O)—$R_4$, where $R_4$ is H or $R_3$ as previously defined;
(4) —C(=O)O—$R_3$, where $R_3$ is as previously defined; and
(5) —C(O)N—$R_6R_7$, where $R_6$ and $R_7$ are as previously defined;

$R_2$ is selected from the group consisting of:
(1) hydroxy protecting group;
(2) $R_5$, where $R_5$ is as previously defined;
(3) —X—Y—$R_5$, where $R_5$ is as previously defined X=—C(O)—, —C(O)O—, —C(O)NH—, or absent, and Y=$C_1$–$C_6$-alkyl, or absent; and
(4) $C_1$–$C_6$-alkyl, $C_2$–$C_6$-alkenyl or $C_2$–$C_6$-alkynyl optionally substituted with one or more substituents selected from the group consisting of:
a. halogen;
b. aryl;
c. substituted aryl;
d. heteroaryl;
e. substituted heteroaryl;
f. —O—$R_5$, where $R_5$ is as previously defined;
g. —O—$C_1$–$C_6$-alkyl-$R_5$, where $R_5$ is as previously defined;

h. —O—$C_2$-$C_6$-alkenyl-$R_5$, where $R_5$ is as previously defined;

i. —O—$C_2$-$C_6$-alkynyl-$R_5$, where $R_5$ is as previously defined; and j. —$NR_6R_7$, where $R_6$ and $R_7$ are as previously defined; and $Rp_1$ is hydrogen or hydroxy protecting group.

3. A compound as defined in claims 1 or 2 or a pharmaceutical ester, salt or prodrug thereof which is selected from the group consisting of:

| | |
|---|---|
| A=—$CH_2CH$=$CH_2$, $R_{P1}$=H, Z=acetyl; | Compound of formula I |
| A=—$CH_2CH$=CH-(3-quinolyl), $R_{P1}$=H, Z=acetyl; | Compound of formula I |
| A=—$CH_2CH_2CH_2$-(3-quinolyl), $R_{P1}$=H, Z=acetyl; | Compound of formula I |
| A=—$CH_2CH_2CH_2$-(3-quinolyl), $R_{P1}$=H, Z=H; | Compound of formula I |
| A=—$CH_2CH$=CH-(3-quinolyl), $R_{P1}$=H, Z=H; | Compound of formula I |
| A=$R_1$=—$CH_2CH$=$CH_2$, $R_{P1}$=H, Z=acetyl; | Compound of formula I |
| A=—$CH_2CH$=$CHCH_2$-(4-phenyl-1-imidazolyl), $R_{P1}$=H, Z=acetyl; | Compound of formula I |
| A=—$CH_2CH_2CH_2CH_2$-(4-phenyl-1-imidazolyl), $R_{P1}$=H, Z=acetyl; | Compound of formula I |
| A=—$CH_2CH_2CH_2CH_2$-(4-phenyl-1-imidazolyl), $R_{P1}$=H, Z=H; | Compound of formula I |
| A=—$CH_2CH_2CH_2CH_2$-(4-phenyl -1-imidazolyl), $R_1$= —$CH_2CH$=$CH_2$, $R_{p1}$=H, Z=acetyl; | Compound of formula I |
| A=—$CH_2CH$=$CHCH_2CH_2$-(4-phenyl-1-imidazolyl), $R_1$=$R_{p1}$=H, Z=acetyl; | Compound of formula I |
| A=—$CH_2CH_2CH_2CH_2CH_2$-(4-phenyl-1-imidazolyl), $R_1$= —$CH_2CH$=$CH_2$, $R_{p1}$=H, Z=acetyl; | Compound of formula I |
| A=—$CH_2CH_2CH_2CH_2$-(4-(3-pyridyl)-1-imidazolyl), $R_{P1}$=H, Z=acetyl; | Compound of formula I |
| A=—$CH_2CH_2CH_2CH_2$-(4-(3-pyridyl)-1-imidazolyl), $R_{P1}$=H, Z=H; | Compound of formula I |
| A=—$CH_2CH_2CH_2CH_2$-(4-(3-pyridyl)-1-imidazolyl), $R_{P1}$=H, $R_{P2}$=—$CH_2CH$=$CH_2$; | Compound of formula I |
| A=—$CH_2CH$=$CH_2$, $R_{P1}$=H, $R_2$=H; | Compound of formula II |
| A=—$CH_2CHCH_2$, $R_2$=—$C(O)CH_2$-(2-pyridyl), $R_{P1}$=H; | Compound of formula II |
| A=—$CH_2CH_2CH_2$-(3-quinolyl), $R_2$=H and $R_{P1}$=H; and | Compound of formula II |
| A=—$CH_2CH_2CH_2$-(3-quinolyl), $R_2$=H, $R_{P1}$=H | Compound of formula II |

4. A pharmaceutical composition for treating bacterial infections comprising a therapeutically effective amount of a compound of claims 1, 2 or 3 or a pharmaceutically acceptable salt, ester or prodrug thereof in combination with a pharmaceutically acceptable carrier.

5. A method for treating bacterial infections comprising administering to a mammal in need of such treatment a pharmaceutical composition comprising a therapeutically-effective amount of a compound of claims 1, 2 or 3 or a pharmaceutically acceptable salt, ester or prodrug thereof.

6. A process for the preparation of a compound represented by formula I, as in claim 1 comprising the steps:

(a) reacting a compound represented by the formula:

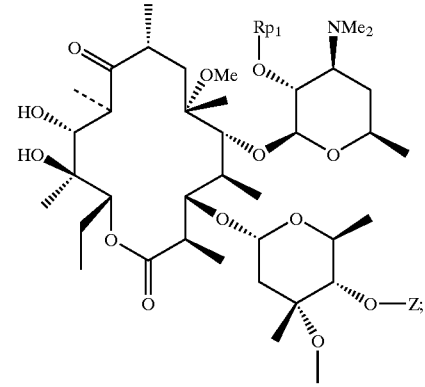

where $Rp_1$ and Z are as defined in claim 1, with a tert-butyl allyl carbonate and a palladium catalyst with a phosphorus ligand in an aprotic solvent to provide a compound represented by the formula:

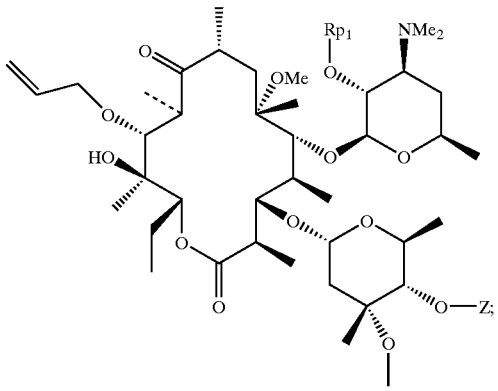

b) reacting the product of step (a) with an aryl halide or an aryl triflate, where the said aryl group is the group R that is selected from a aryl, heteroaryl, substituted aryl, or substituted heteroaryl group, in the presence of a palladium catalyst with a phosphorus ligand to provide a compound represented by the formula:

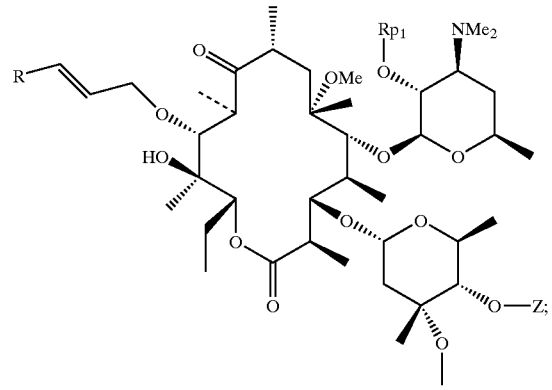

(c) the product of step (b) is optionally first hydrogenated, with palladium on carbon under hydrogen at a temperature between 0° C. to 50° C., or directly treated with methanol from 0° C. to 60° C. to provide a compound represented by the formula:

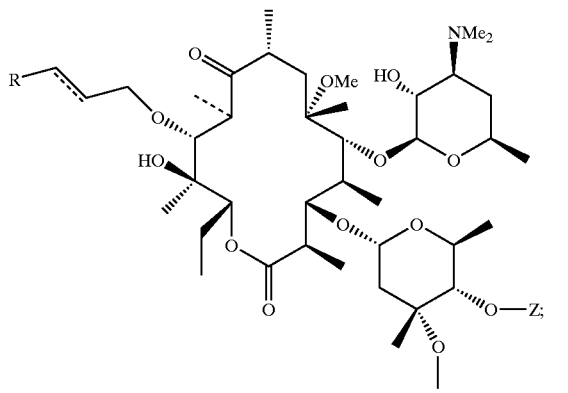

(d) the product of step (c) is then further deprotected by acid hydrolysis, base hydrolysis, tetrabutylammonium fluoride or hydrofluoric acid to provide a compound represented by formula I in claim 1, where A=—CH$_2$CH=CHR or —CH$_2$CH$_2$CH$_2$R, and R$_1$, Rp$_1$ and Z are each H.

7. A process for the preparation of a compound represented by formula I, as in claim 1 comprising the steps:

(a) reacting a compound represented by the formula:

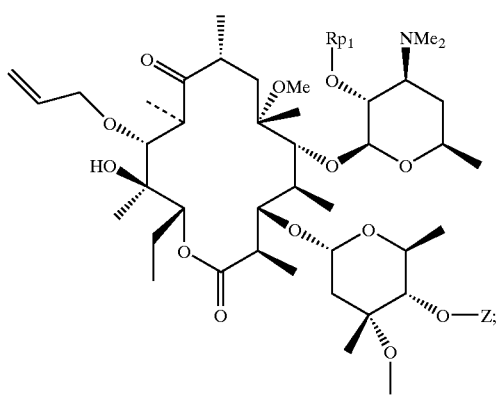

where Rp$_1$ and Z are as defined in claim 1, with an aryl-alkenyl derivative of the formula R—(CH$_2$)$_n$—CH=CH, where n=1, 2 or 3, using ruthenium catalysts, where the said R group is selected from an aryl, heteroaryl, substituted aryl, or substituted heteroaryl group, at a temperature between 0° C. to 50° C. in an aprotic solvent to provide a compound represented by the formula:

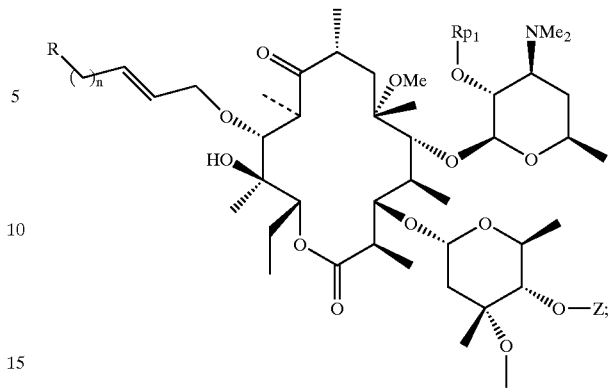

(b) the product of step (a) is optionally first hydrogenated, with palladium on carbon under hydrogen at a temperature between 0° C. to 50° C., or directly treated with methanol from 0° C. to 60° C. to provide a compound represented by the formula:

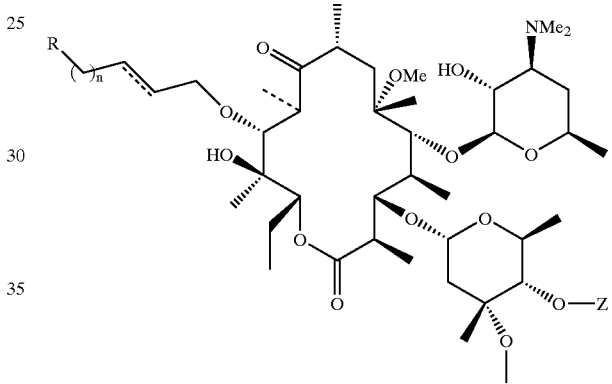

(c) the product of step (b) is then further deprotected by acid hydrolysis, base hydrolysis, tetrabutylammonium fluoride or hydrofluoric acid to provide a compound represented by Formula I in claim 1, where A=—CH$_2$CH=CH(CH$_2$)$_n$R or —CH$_2$CH$_2$CH$_2$(CH$_2$)$_n$R when n=1, 2 or 3, and R$_1$, Rp$_1$ and Z are each H.

8. A process for the preparation of a compound represented by formula I, as in claim 1 comprising the steps:

(a) reacting a compound represented by the formula:

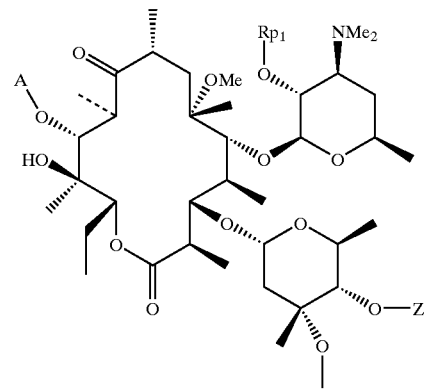

where A, $Rp_1$ and Z are as defined in claim 1, with a tert-butyl allyl carbonate catalyzed by a palladium catalyst with a phosphorus ligand in an aprotic solvent for 30 to 40 hours at a temperature between room temperature to 100° C. to provide a compound represented by the formula:

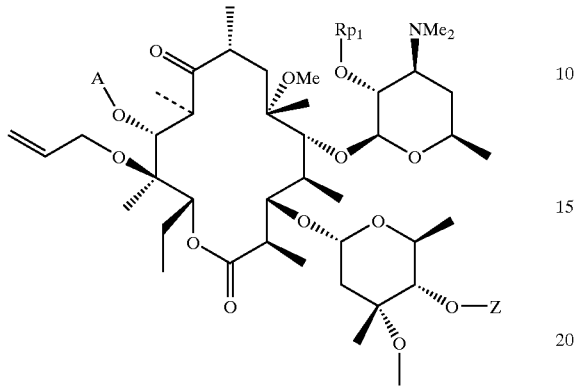

(b) the product of step (a) is treated with methanol from 0° C. to 60° C. to provide a compound represented by the formula:

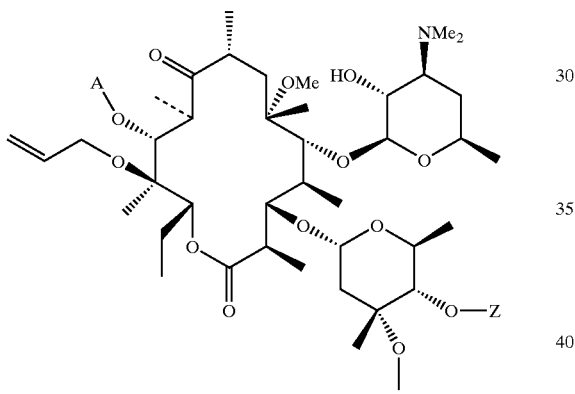

(c) the product of step (c) is then further deprotected by acid hydrolysis, base hydrolysis, tetrabutylammonium fluoride or hydrofluoric acid to provide a compound represented by formula I in claim 1, where A is as defined in claim 1, $R_1$=—$CH_2CH$=$CH$, and $Rp_1$ and Z are each H.

9. A process for the preparation of a compound represented formula II, as in claim 2 comprising the steps:

(a) reacting a compound represented by the formula:

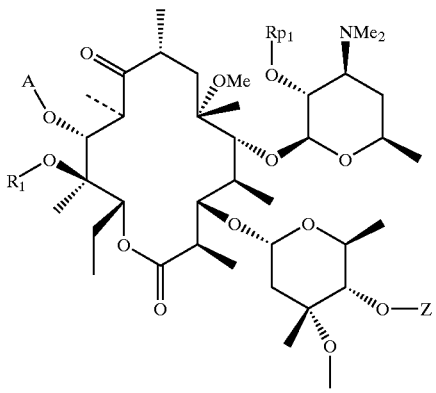

where A, $R_1$, $Rp_1$ and Z are as defined in claim 2, with dilute aqueous acid at a temperature between 0° C. to 70° C. to provide a compound represented by the formula:

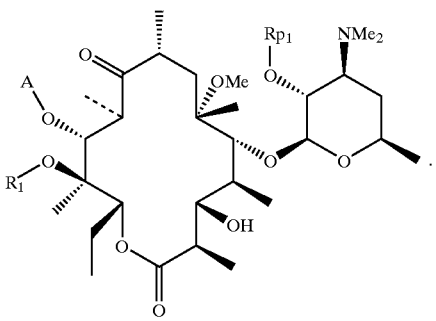

* * * * *